United States Patent
Jessop et al.

(10) Patent No.: US 9,801,370 B2
(45) Date of Patent: *Oct. 31, 2017

(54) CONTROL OF ARTHROPOD INFESTATION

(71) Applicant: Exosect Limited, Winchester, Hants (GB)

(72) Inventors: Nicholas Hugh Hylton Jessop, Winchester (GB); Adam Nunn, Winchester (GB)

(73) Assignee: Exosect Limited, Winchester, Hants (GB)

( * ) Notice: Subject to any disclaimer, the term of this patent is extended or adjusted under 35 U.S.C. 154(b) by 175 days.

This patent is subject to a terminal disclaimer.

(21) Appl. No.: 14/418,155

(22) PCT Filed: Jul. 29, 2013

(86) PCT No.: PCT/GB2013/000327
§ 371 (c)(1),
(2) Date: Jan. 29, 2015

(87) PCT Pub. No.: WO2014/020295
PCT Pub. Date: Feb. 6, 2014

(65) Prior Publication Data
US 2015/0150250 A1    Jun. 4, 2015

(30) Foreign Application Priority Data

Aug. 1, 2012 (GB) .................................. 1213740.2
Feb. 6, 2013 (GB) .................................. 1302145.6

(51) Int. Cl.
*A01N 25/24* (2006.01)
*A01N 57/16* (2006.01)
*A01N 25/08* (2006.01)
*A01N 25/12* (2006.01)
*A01N 25/26* (2006.01)
*A01N 25/28* (2006.01)

(52) U.S. Cl.
CPC ............. *A01N 25/24* (2013.01); *A01N 25/08* (2013.01); *A01N 25/12* (2013.01); *A01N 25/26* (2013.01); *A01N 25/28* (2013.01); *A01N 57/16* (2013.01)

(58) Field of Classification Search
CPC .................................................... A01N 25/24
See application file for complete search history.

(56) References Cited

U.S. PATENT DOCUMENTS

2012/0156273 A1    6/2012  Gutsmann et al.

FOREIGN PATENT DOCUMENTS

| GB | 2480899 A | 12/2011 | |
| GB | 2481307 A | 12/2011 | |
| GB | WO 2011148144 A1 * | 12/2011 | ............ A01N 25/04 |
| GB | 2481881 A | 1/2012 | |
| GB | 2482900 A | 2/2012 | |
| GB | 2490242 A | 10/2012 | |
| WO | 97/27939 A1 | 8/1997 | |
| WO | 2011/128639 A2 | 10/2011 | |
| WO | 2011/157983 A1 | 12/2011 | |
| WO | 2012/157983 A2 | 11/2012 | |

OTHER PUBLICATIONS

International Search Report for PCT/GB2013/000327 dated Nov. 5, 2013.
Communication dated Dec. 6, 2013 from the Intellectual Property Office of the UK issued in Application No. GB1302145.6.
Communication dated Nov. 30, 2012 from the Intellectual Property Office of the UK issued in Application No. GB1213740.2.

* cited by examiner

*Primary Examiner* — Noble Jarrell
*Assistant Examiner* — John S Kenyon
(74) *Attorney, Agent, or Firm* — Sughrue Mion, PLLC

(57) ABSTRACT

Use of particles in controlling a population of arthropod pests, wherein the particles comprise i) a hydrophobic exterior that adheres to the cuticle of at least one species of an arthropod pest; and ii) at least one pesticide associated with the said particles, wherein the pesticide is present at a weight of no more than 2% of the weight of the particles, populations of particles, methods of producing populations of particles and methods of application of such populations.

15 Claims, 2 Drawing Sheets

CONTROL OF ARTHROPOD INFESTATION

CROSS REFERENCE TO RELATED APPLICATIONS

Figure 1:
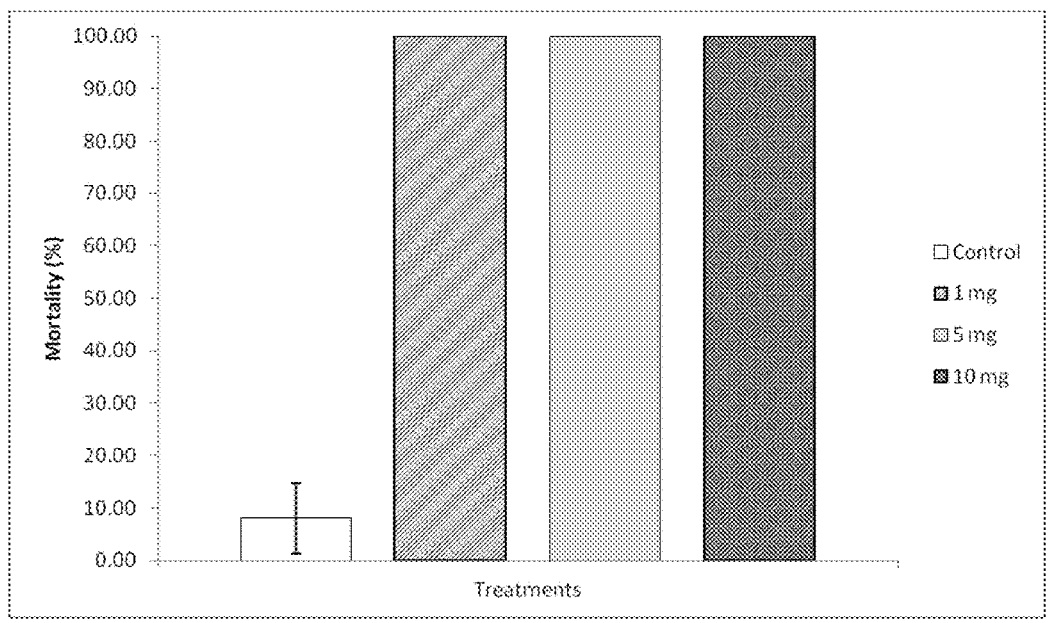

This application is a National Stage of International Application No. PCT/GB2013/000327 filed Jul. 29, 2013, claiming priority based on Great Britain Patent Application Nos. 12 13 740.2, filed Aug. 1, 2012 and 13 02 145.6, filed Feb. 6, 2013, the contents of all of which are incorporated herein by reference in their entirety.

The present invention relates to particulate formulations for controlling arthropod infestation, compositions for treating arthropod infestation and uses thereof. In particular, the invention relates to methods of controlling arthropod infestation on crop plants, arthropod infestation in or on stored produce, uses of arthropodicidal compositions in particulate form, populations of particles comprising arthropodicides in association with hydrophobic surfaces, methods of producing such populations, and uses thereof.

A major drawback of using synthetic or natural chemicals on growing crops to control arthropod infestation is that applied chemicals are applied at relatively high concentrations. Once applied, such chemicals tend to sit in the environment post-application, and while being useful in controlling or in preventing arthropod infestation it is known that the chemical load to the environment can be high, and as a consequence other life forms including man can suffer. Furthermore, when chemicals are applied to produce such as vegetable parts or fruit, or to dried produce such as grain destined for consumption in fresh or in processed form by humans and/or animals e.g. livestock, it is known that chemical loads associated with the produce get into the food supply. Chemical residues typically remain on food produce even after conventional washing procedures have been applied.

With the increase in inter alia the human population since the second world war, the use of chemicals in agriculture is ever-growing. While the use of chemicals is necessary to control infestation by arthropod pests, it is now recognised that the chemical load to the environment and/or on end food products should be lowered.

Chemicals that are applied to food produce are implicated as causative agents for disease, such as skin diseases and cancers. While the use of chemicals for arthropod pest control has obvious benefits in terms of preserving crop yield and food supplies, there exists a need to reduce the level of chemical residues found on crop products while maintaining an acceptable level of protection against arthropod pests.

It has now been found that the amount of pesticide that is required for efficient control of arthropod infestation of crop-related produce such as seeds and grain storage produce, growing crops and crop produce such as fruits and vegetable parts can be very much lower when presented to such sites on particles of the invention than that required using conventional means of application of pesticides for controlling arthropod infestation on such crop-related produce.

It is an object of the present invention to provide a more efficient means of controlling arthropod pests on crop-related produce while maintaining efficient control against such pests.

It is a further object of the present invention to provide formulations that contain lesser amounts of chemicals such as insecticides and the like for controlling arthropod pests on crop-related produce such as growing crops and/or on stored produce. These and other objects of the invention will become apparent from the following description and examples.

According to the present invention there is provided use of particles in controlling a population of arthropod pests on growing crops and/or produce thereof, wherein the particles comprise i) an hydrophobic exterior that adheres to the cuticle of at least one species of an arthropod pest; and ii) at least one pesticide associated with the said particles, wherein the pesticide is present at a weight of no more than 2% of the weight of the particles.

It has now been found that particles employed in the invention act to potentiate or enhance the action of pesticide on target arthropod pests when the pesticide is present at a weight of no more than 2.00% of the weight of the particles, for example from ≥0.1% to ≤2%, ≥0.2% to ≤2%, ≥0.25% to ≤2%, ≥0.50% to ≤2%, or any value inbetween 0.1% to 2% of the weight of the particles. Other pesticide weight values include ≤1.00%, such as ≤0.75%, ≤0.50%, or ≤0.25% of the weight of the particles, or at any value from 0.1% to 2% of the weight of the particles, depending on the active agent used. The man skilled in the art will appreciate that the amount of active agent used in conjunction with the particles as described herein is lower than the amount of active agent applied and retained per unit area (on a crop or on the surfaces of vegetables or fruit) or applied and retained per unit volume of seed (e.g. in a grain mass) applied conventionally, and hence the use of particles of the invention provides a more efficient means with which to apply pesticides to control arthropod infestations of crop-related produce as alluded to herein.

Generally, the particles of use in the invention possess a volume mean diameter (VMD) that enables them to adhere to the cuticle of at least one species of arthropod pest and/or to adhere to the surface of plants, surfaces found in storage facilities and on stored dry produce such as grain. The VMD of the particles used in the invention may be any size suitable for use in the invention, for example, in the range up to 500 μm, for example up to 300 μm. Preferably, the VMD of particles of use in the invention is up to 100 μm or 200 μm and may be up to 50 μm, for example in the range from 5 μm to 50 μm or any size thereinbetween such as 6 μm, 7 μm, 8 μm, 9 μm, 10 μm, 11 μm, 12 μm, 13 μm, 14 μm, 15 μm, 16 μm, 17 μm, 18 μm, 19 μm, 20 μm and so on. The volume mean diameter of particles of use in the invention is typically ≥10 μm or ≥12 μm and may lie in the range from 10 μm to 200 μm and may have a value that lies anywhere thereinbetween.

The particles may comprise layered particles, for example they may have a metallic core such as a magnetic metal core, or a core made up of an inorganic powder such as kaolin or talc, or a core made of a suitable substrate such as substrate that is inert with respect to the outer exterior layer, such as rubber. Such particles consisting of a core that is not a material that is similar to the material of the outermost external layer will have an external hydrophobic layer applied that is capable of adhering to the cuticle of a pest arthropod. Typically, the hydrophobic layer is made up of a natural, synthetic, or mineral wax or a mixture of two or more thereof. Such waxes making up the hydrophobic layer typically have a melting point ≥40° C. or ≥50° C., more preferably a melting point above of ≥60° C. or preferably ≥70° C. Waxes of use in the invention include waxes from one or more species of waxes selected from the group consisting of natural, synthetic and mineral waxes. Typically, waxes of use in the invention have a melting temperature of ≥40° C., depending on design. Suitable waxes of use in the invention include a mixture of one or more waxes having a melting point of preferably ≥50° C., and most preferably are made up of hard waxes having a melting point of ≥70° C. Examples of natural waxes of use in the present invention include carnauba wax, beeswax, Chinese wax, shellac wax, spermaceti wax, myricyl palmitate, cetyl palmitate, candelilla wax, castor wax, ouricury wax, wool wax, sugar cane wax, retamo wax, rice bran wax or mixtures of two or more thereof.

Synthetic waxes of use in the present invention include suitable waxes selected from paraffin wax, microcrystalline wax, Polyethylene waxes, Fischer-Tropsch waxes, substituted amide waxes, polymerized α-olefins and the like.

Mineral waxes of use in the invention include montan wax (e.g. Luwax® BASF) ceresin wax, ozocerite, peat wax and the like.

Preferably, waxes of use in the invention are selected from carnauba wax and montan wax or a mixture thereof.

In a further preferment of the invention, there is provided use of particles comprising solid wax particles, that is to say, particles that are made up of at least one wax that do not have cores consisting of other materials other than waxes that are selected from one or more species of waxes from the group consisting of natural, synthetic and mineral waxes. Typically, waxes of use in the invention have a melting temperature of ≥40° C., depending on design. Suitable waxes of use in the invention include waxes having a melting point of preferably ≥50° C., and most preferably are made up of hard waxes having a melting point of ≥70° C. Examples of natural waxes of use in the present invention include carnauba wax, beeswax, Chinese wax, shellac wax, spermaceti wax, myricyl palmitate, cetyl palmitate, candelilla wax, castor wax, ouricury wax, wool wax, sugar cane wax, retamo wax, rice bran wax and mixtures of two or more thereof.

Synthetic waxes of use in the present invention include suitable waxes selected from paraffin wax, microcrystalline wax, Polyethylene waxes, Fischer-Tropsch waxes, substituted amide waxes, polymerized α-olefins and the like.

Mineral waxes of use in the invention include montan wax (e.g. Luwax® BASF) ceresin wax, ozocerite, peat wax and the like.

Such solid wax particles are preferably made up of carnauba wax or montan wax or a mixture thereof.

Particles of the invention may be loaded with or associated with at least one pesticide of choice. Suitable pesticides may be selected from pyrethroids, spinosyns, carbamates, gamma amino butyric acid (GABA) inhibitors, neonicotinoids, anthranilamides, formonetins, essential oils, insect growth regulators and organophosphates or mixtures of two or more thereof. Examples of suitable chemicals of use in the invention may be selected from the pyrethroids, such as α-cypermethrin, λ-cyhalothrin, [cyano-(3-phenoxyphenyl)-methyl] 3-(2,2-dibromoethenyl)-2,2-dimethyl-cyclopropane-1-carboxylate (deltamethrin), and τ-fluvalinate, the organophosphates such as chlorpyriphos (diethoxy-sulfanylidene-(3,5,6-trichloropyridin-2-yl)oxy-l^{5}-phosphane), malathion (diethyl 2 dimethoxyphosphino-thioyl-sulfanylbutanedioate), coumaphos (3-chloro-7-diethoxyphosphinothioyloxy-4-methylcoumarin), Pirimiphos-methyl (O-2-diethylamino-6-methylpyrimidin-4-yl-O,Odimethylphosphorothioate) and stirifos ([(E)-2-chloro-1-(2,4,5-trichlorophenyl)ethenyl]dimethyl phosphate) the carbamates such as amitraz (N-(2,4-dimethylphenyl)-N-[(2,4-dimethylphenyl)iminomethyl]-N-methylmethanimidamide), the spinosans such as spinosad (Dow Agrichemical, France), the gamma amino butyric acid (GABA) inhibitors such as fipronil (5-amino-1-[2,6-dichloro-4-(trifluoromethyl)phenyl]-4 (trifluoromethylsulfinyl) pyrazole-3-carbonitrile), the neonicotinoids such as imidacloprid (N-[1-[(6-Chloro-3-pyridyl)methyl]-4,5-dihydroimidazol-2-yl]nitramide), the anthranilamides, the formononetins such as 7-Hydroxy-3-(4-methoxyphenyl) chromone, the essential oils such as tea tree oil, thyme oil (and derivatives such as thymol), citronella oil, and menthol, and the insect growth regulators such as methoxyfenozide (N-tert-butyl-N'-(3-methoxy-o-toluoyl)-3,5-xylohydrazide) and the like. Further pesticides that may be used in the invention include Allethrin stereoisomers, Bifenthrin, Beta-Cyfluthrin, Cyfluthrin, Cypermethrin, Cyphenothrin, Deltamethrin, Esfenvalerate, Fenpropathrin, Lambda-Cyhalothrin, Gamma Cyhalothrin, Imiprothrin, 1RS cis-Permethrin, Permethrin, Prallethrin, Resmethrin, Sumithrin (d-phenothrin), Tefluthrin, Tetramethrin, Tralomethrin, and Zeta-Cypermethrin. It is known that pyrethrins and other pyrethroid products may be formulated with synergists, such as piperonyl butoxide and MGK-264, to enhance the pesticidal properties of the product. Such synergists typically have no pesticidal effects of their own but enhance the effectiveness of other chemicals.

Preferred compounds for use in particle formulations of the invention include those selected from the group consisting of pyrethroids such as such as deltamethrin and tau-fluvalinate (Mavrik), organophosphates such as Actellic (active ingredient pirimiphos-methyl), the spinosyns such as spinetoram (Dow Agrosciences), the major component being 3'ethoxy, 5,6-dihydro spinosyn J ((2R,3aR,5aR,5bS, 9S,13S,14R,16aS,16bR)-13-{[(2S,5S,6R)-5-(dimethylamino)-6-methyltetrahydro-2Hpyran-2-yl]oxy}-9-ethyl-14-methyl-7,15-dioxo-2,3,3a,4,5,5a,5b,6,7,9,10,11,12,13,14, 15,16a,16b-octadecahydro-1H-as-indaceno[3,2-d] oxacyclododecin-2-yl 6-deoxy-3-O-ethyl-2,4-di-O-methyl-beta-L-mannopyranoside), and minor component being 3'ethoxy spinosyn L: ((2S,3aR,5aS,5bS,9S,13S,14R,16aS, 16bS)-13-{[(2S,5S,6R)-5-(dimethylamino)-6-methyltetrahydro-2H-pyran-2-yl]oxy}-9-ethyl-4,14-dimethyl-7,15-di-oxo-2,3,3a,5a,5b,6,7,9,10,11,12,13,14,15,16a,16b-hexadecahydro-1H-as-indaceno[3,2-d]oxacyclododecin-2-yl 6-deoxy-3-O-ethyl-2,4-di-O-methyl-beta-L-mannopyranoside)), and organophosphates or mixtures of two or more thereof.

Particles of use in the invention are selected on the basis of the active agent employed and such particles may be used against any arthropod crop or storage pest of interest including but not limited to those selected from the group consisting of Saw-toothed Grain Beetle (*Oryzaephilus surinamensis*), Grain Weevil (*Sitophilus granarius*), Common Flour Mite (*Acarus siro*), Warehouse Moth (*Ephestia elutella*), Flour or Mill Moth (*Ephestia kuhniella*), Flour Beetles (*Tribolium* spp.), Rust-red Grain Beetle (*Cryptolestes ferrugineus*) and Cosmopolitan Food Mite (*Glycyphagus destructor*), codling moth, *Cydia pomonella*; oriental fruit moth, *Grapholita molesta*; armyworms from *Spodoptera* spp.; cabbage looper, *Trichoplusia ni*; thrips, *Frankliniella* spp.), onion thrips (*Thrips tabaci*); leafminers (*Liriomyza* spp.); Corn earworm, *Helicoverpa zea*, European cornborer, *Ostrinia nubilalis; Agrotis* spp.; Cotton Bollworms, *Helicoverpa* spp.; armyworms, Soybean looper, *Pseudoplusia includens*; Apple maggot, *Rhagoletis pomonella*; Pear psylla, *Cacopsylla* spp.; Navel orangeworm, *Amyelois transitella*; Tree Nuts Codling moth; Crucifers Diamondback moth, *Plutella xylostella*; cabbage worms, *Pieris* spp.; Grape berry moth, *Lobesia botrana*; Cucurbits Pickleworm, *Diaphania* spp.; and psocids, such as book lice.

In the treatment of grain and dry foodstuffs, such as milled grain the active agent of choice is selected from those that are effective against one or more species of arthropod pest typically selected from the group Saw-toothed Grain Beetle (*Oryzaephilus surinamensis*), Grain Weevil (*Sitophilus granarius*), Common Flour Mite (*Acarus siro*), Warehouse Moth (*Ephestia elutella*), Flour or Mill Moth (*Ephestia kuhniella*), Flour Beetles (*Tribolium* spp.), Rust-red Grain Beetle (*Cryptolestes ferrugineus*) and Cosmopolitan Food Mite (*Glycyphagus destructor*).

Naturally, the skilled addressee will appreciate that the selection of active agent will be determined by the species of chemical most appropriate for applying to the crop, crop produce, storage area, or grain mass for arthropod pest population control.

By making use of the hydrophobicity of the hydrophobic layer and of the electrostatic attraction of the carrier particles of use in the invention an efficient carrier system is achieved that is able to carry lesser amounts of chemical to target surfaces, such as plant surfaces, arthropod surfaces, dried food surfaces such as those of beans, lentils and peas, cereal grain seeds such as wheat, barley and rye, and food storage surfaces in food storage areas.

The particles of use in the invention may also contain suitable excipients commonly employed in the art such as flow agents or anti-caking agents selected from sodium bicarbonate, sodium ferrocyanide, potassium ferrocyanide, calcium ferrocyanide, bone phosphate, sodium silicate, silicon dioxide, calcium silicate, magnesium trisilicate, talcum powder, sodium aluminosilicate, potassium aluminium silicate, calcium aluminosilicate, bentonite, aluminium silicate, stearic acid, polydimethylsiloxane and the like.

Additionally, particles of use in the invention may contain other components such as additives selected from UV blockers such as beta-carotene or p-aminobenzoic acid, colouring agents such as optical brighteners and commercially available colouring agents, such as food colouring agents, plasticisers such as glycerine or soy oil, antimicrobials such as potassium sorbate, nitrates, nitrites, propylene oxide and the like, antioxidants such as vitamin E, butylated hydroxyl anisole (BHA), butylated hydroxytoluene (BHT), and other antioxidants that may be present, or mixtures thereof. The skilled artisan will appreciate that the selection of such commonly included additives will be made depending on end purpose, and perceived need.

The particles of use in the invention should be effective in controlling populations of pests such as grain storage arthropods as herein defined.

"Grain storage areas" for the purposes of the present invention includes dried food and/or grain storage sites such as grain silos and grain bins where dried food or grain is stored immediately after harvest or prior to processing and includes warehouses where dried food and grain is stored prior to shipment, and transport facilities such as those of shipping containers, the holds of ships, trucks, aeroplanes, storage areas in supermarkets, dried food holding centres and the like. The term "grain storage area" includes within its ambit those storage areas in which harvested grain products such as wheat, rye, barley, corn, sorghum grains, and dried foods such as flours, dried beans, lentils, rice and other foodstuff commodities such as dried pasta derived from grain and/or other dried foodstuffs are held.

For the purposes of the present invention "controlling arthopod pests" means that the arthropod population to which particles of use in the invention are applied are ones that suffer losses due to death, ill health that may ultimately lead to death, and/or inability to reproduce or reduction in the ability to reproduce. Preferably, the controlling of populations of storage arthropods means that at least 80%, preferably 90% or more of the population of arthropods dies within a few days of application of compositions of the invention. Preferably, the populations of arthropods that are adversely affected by compositions of the invention die or at least suffer sub-lethal effects which contribute to long-term population reduction as a result of the application of particles of use in the invention to the crop in the field; to a stored mass of produce such as a grain mass or to storage areas, such as grain storage areas. The man skilled in the art will appreciate that the population of pest arthropods to which the particles of use in the invention are applied may be made up of one or more than one species of pest arthropod. Examples of species of arthropods that may make up a population of pest arthropods include grain storage arthropods that may be affected by particles of use in the invention include grain storage beetles such as *Oryzaephilus surinamensis* (saw-toothed grain beetle), *Sitophilus granarius* (grain weevil), *Cryptolestes ferrugineus* (rust-red grain beetle), Common Flour Mite (*Acarus siro*), Warehouse Moth (*Ephestia elutella*), Flour or Mill Moth (*Ephestia kuhniella*), Flour Beetles (*Tribolium* spp.) and Cosmopolitan Food Mite (*Glycyphagus destructor*).

Suitable waxes of use in the invention include waxes selected from natural, synthetic and mineral waxes. Typically, waxes of use in the invention have a melting temperature of $\geq 40°$ C., depending on design. Suitable waxes of use in the invention include waxes having a melting point of preferably $\geq 50°$ C., and most preferably are made up of hard waxes having a melting point of $\geq 70°$ C. Examples of natural waxes of use in the present invention include carnauba wax, beeswax, Chinese wax, shellac wax, spermaceti wax, myricyl palmitate, cetyl palmitate, candelilla wax, castor wax, ouricury wax, wool wax, sugar cane wax, retamo wax, rice bran wax or mixtures of two or more thereof.

Synthetic waxes of use in the present invention include suitable waxes selected from paraffin wax, microcrystalline wax, Polyethylene waxes, Fischer-Tropsch waxes, substituted amide waxes, polymerized α-olefins and the like.

Mineral waxes of use in the invention include montan wax (e.g. Luwax® BASF) ceresin wax, ozocerite, peat wax and the like.

In a preferment of the invention there is provided use of particles in controlling a population of grain storage pests wherein the particles comprise i) an hydrophobic exterior that adheres to the cuticle of at least one species of an arthropod pest; and ii) at least one pesticide associated with the said particles, wherein the pesticide is present at a weight of no more than 2% of the weight of the particles.

As a further aspect of the invention, particles are provided comprising i) an hydrophobic exterior that adheres to the cuticle of at least one species of an arthropod pest; and ii) at least one pesticide associated with the said particles, wherein the pesticide is present at a weight of no more than 2% of the weight of the particles. Particles of the invention may include for example from $\geq 1\%$ to $\leq 2\%$, $\geq 0.2\%$ to $\leq 2\%$, $\geq 0.25\%$ to $\leq 2\%$, $\geq 0.50\%$ to $\leq 2\%$, or any value inbetween 0.1% to $\leq 2\%$ of the weight of the particles. Other pesticide weight values include $\leq 1.00\%$, such as $\leq 0.75\%$, $\leq 0.50\%$, or $\leq 0.25\%$ of the weight of the particles, or at any value from 0.1% to 2% of the weight of the particles, depending on design and/or the active agent used.

In a further aspect of the invention there is provided a method of controlling grain storage arthropod infestation in a grain storage area wherein particles according to the invention are presented to the surfaces of a grain storage area by
i) collecting the composite particles in a dusting apparatus;
ii) releasing the said particles from the said dusting apparatus and into the said grain storage area.

In another aspect of the invention there is provided a method of controlling grain storage arthropod infestation in a grain storage area wherein particles according to the invention are presented to the surfaces of a grain storage area.

In a further aspect of the invention there is provided a population of particles that is effective in controlling populations of arthropod pests comprising particles i) having a hydrophobic exterior that adheres to the cuticle of at least one species of an arthropod pest; and ii) at least one pesticide associated with the said particles, wherein the pesticide is present at a weight of no more than 2% of the weight of the particles.

Particles employed in the invention act to potentiate or enhance the action of pesticide on target arthropod pests when the pesticide is present on the particles at a weight of no more than 2% of the weight of the particles, for example from ≥0.1% to ≤2%, ≥1%, to ≤2%, or any value between 0.1% up to a weight of ≤2%, such as ≥0.1% to ≤1.5% or ≥0.1% to ≤1% of the weight of the particles. Other particles of the invention may include pesticide at a weight of ≤2% of the weight of the particles, such as between 0.1% and 2% of the weight of the particles such as at a weight of ≤1% by weight, such as ≤0.75%, ≤0.50% or ≤0.25% of the weight of the particles, or at any value from 0.1% to 2% of the weight of the particles, depending on the active agent used. The man skilled in the art will appreciate that the amount of active agent used in conjunction with the particles as described herein will be lower than the amount of active agent applied per unit area (on a crop or on the surfaces of vegetables or fruit) or per unit volume (e.g. in a grain mass) applied conventionally, and hence the use of particles of the invention gives rise to a more efficient means with which to apply pesticides to control arthropod infestation.

Generally, the particles of use in the invention possess a volume mean diameter (VMD) that enables them to adhere to the cuticle of at least one species of arthropod pest and/or to adhere to the surface of plants, surfaces found in storage facilities and on stored dry produce such as grain. The VMD of the particles used in the invention may be any size suitable for use in the invention, for example, in the range up to 500 μm, for example up to 300 μm. Preferably, the VMD of particles of use in the invention is up to 100 μm and may be up to 50 μm, for example in the range from 5 μm to 50 μm or any size thereinbetween such as 6 μm, 7 μm, 8 μm, 9 μm, 10 μm, 11 μm, 12 μm, 13 μm, 14 μm, 15 μm, 16 μm, 17 μm, 18 μm, 19 μm, 20 μm and so on. The volume mean diameter of particles of use in the invention is typically ≥10 μm or ≥12 μm and may lie in the range from 10 μm to 200 μm and may have a value that lies anywhere thereinbetween.

A population of particles of use in the invention typically an hydrophobic exterior that comprises a wax that is selected from one or more species of waxes selected from the group consisting of waxes selected from natural, synthetic and mineral waxes. Typically, waxes of use in a population of particles of the invention have a melting temperature of ≥40° C., depending on design. Suitable waxes of use in the invention include waxes having a melting point of preferably ≥50° C., and most preferably are made up of hard waxes having a melting point of ≥70° C. Examples of natural waxes of use in the present invention include carnauba wax, beeswax, Chinese wax, shellac wax, spermaceti wax, myricyl palmitate, cetyl palmitate, candelilla wax, castor wax, ouricury wax, wool wax, sugar cane wax, retamo wax, rice bran wax or a mixture of two or more thereof. Preferably, the particles comprise waxes selected from carnauba wax and montan wax or a mixture thereof.

Synthetic waxes of use in the present invention include suitable waxes selected from paraffin wax, microcrystalline wax, Polyethylene waxes, Fischer-Tropsch waxes, substituted amide waxes, polymerized α-olefins and the like.

Mineral waxes of use in the invention include montan wax (e.g. Luwax® BASF) ceresin wax, ozocerite, peat wax and the like.

A population of particles of the invention may include a pesticide effective against arthropod pests selected from the group consisting of pyrethroids, spinosyns, carbamates, gamma amino butyric acid (GABA) inhibitors, neonicotinoids, anthranilamides, formonetins, essential oils, insect growth regulators and organophosphates or mixtures of two or more thereof. Preferably, the pesticide is selected from pyrethroids, spinosyns, and organophosphates or mixtures of two or more thereof.

In a further aspect of the invention, there is provided use of a population of particles of the invention in the control of grain storage arthropod infestation in grain storage areas.

In a further aspect of the invention, there is provided a method of producing a population of particles as defined herein comprising the steps of
i) collecting particles having an hydrophobic exterior of a volume mean diameter up to 200 μm; and
ii) admixing pesticide with the said particles.

In a preferment of the invention, there is provided a method of controlling grain storage arthropod infestation in a grain storage area wherein a population of particles as defined herein are presented to the surfaces of a grain storage area by
i) collecting the particles in a dusting apparatus;
ii) releasing the said particles from the said dusting apparatus and into the said grain storage area.

In a preferment of the invention, there is provided a method of controlling grain storage arthropod infestation in a grain storage area wherein a population of particles as defined herein is presented to the surfaces of a grain storage area.

There now follow examples and figures illustrating the invention. It is to be understood that the teaching of the examples and figures is not to be construed as limiting the invention in any way.

FIGURES

FIG. 1: Percentage mortality of *Oryzaephilus surinamensis* in treatments of 1% Pirimiphos-methyl in Entostat (w/w) after 48 hours of exposure. The results indicate that 100% mortality was achieved in all treatments containing pirimiphos-methyl with no variance and a standard deviation of 0%. The control shows a mean mortality of 8% and a standard deviation of 6.71%.

Figure 2:
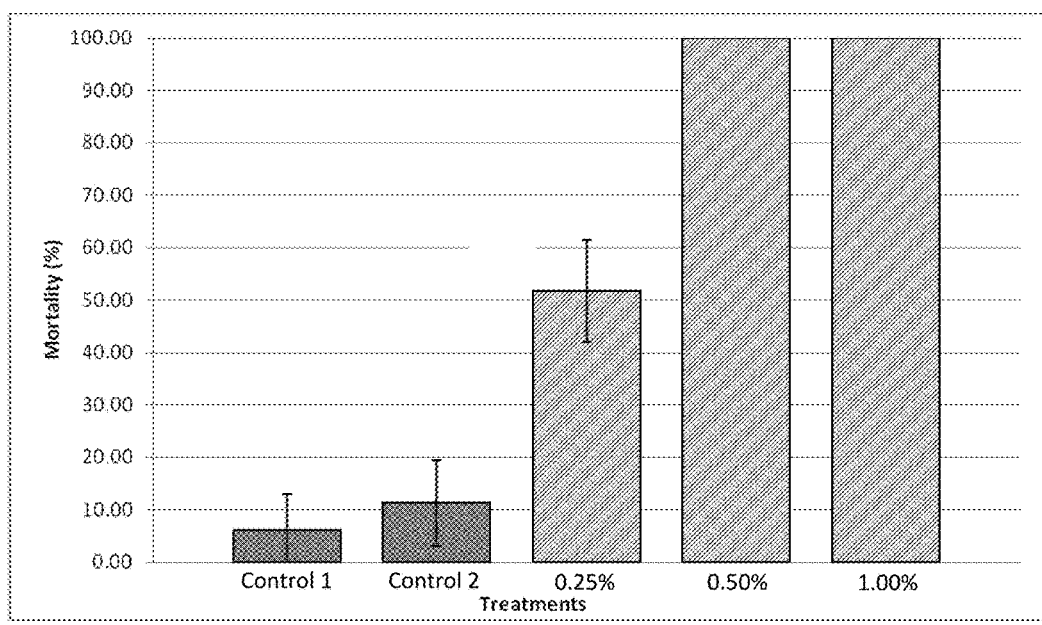

FIG. 2: Graph to show the percentage mortality of *O. surinamensis* in different concentration treatments of pirimiphos-methyl in Entostat (w/w) after 48 hours of exposure. Control 1 represents the untreated control and Control 2 represents the vehicle control. The results indicate that 100% mortality was achieved in treatments containing 1% and 0.5% pirimiphos-methyl, with no variance and a standard deviation of 0% for both. The 0.25% treatment has a mean mortality of 51.75% with a standard deviation of 9.68%. The untreated control shows a mean mortality of 6.16% and a standard deviation of 6.80%, whilst the vehicle control shows a mean mortality of 11.33% with a standard deviation of 8.18%.

EXAMPLES SECTION 1

Efficacy of Different Application Rates of 1% Pirimiphos-Methyl in Entostat (w/w) when Used Against *Oryzaephilus surinamensis* in Grain

1. OBJECTIVE

The purpose of the study was to examine the influence of application rate in grain on the efficacy of 1% Pirimiphos-methyl in Entostat (w/w) against *Oryzaephilus surinamensis* (sawtooth grain beetle). Rates examined were equivalent to 200 g, 100 g, and 20 g of powder per 1000 kg of grain.

2. STUDY OUTLINE

Actellic is an organophosphate insecticide originally developed by Imperial Chemical Industries (now Syngenta) in 1967. It uses pirimiphos-methyl as its active ingredient. It is highly efficacious against a range of insect species and up until recently has been successfully used for the control of insect pests in stored grain and a range of public health situations. New regulations have resulted in the withdrawal of support for Actellic due to concerns over mammalian toxicity, environmental persistence and operator overexposure. Therefore any new formulations that are able to maintain a high efficacy whilst reducing the concentration of active ingredient are sought after.

The present study examined the influence of application rate in grain on the efficacy of 1% Pirimiphos-methyl in Entostat (w/w) against *O. surinamensis*. To gather this information, quantities of grain were treated with four separate treatments of powder (inclusive of negative control), homogenised, and split into samples before the addition of the beetles. The beetles were to be maintained within the grain for two weeks or until ~95% mortality was achieved, with mortality checks at 48 hour time points. However, in actuality only one time point check was required.

Methods

3. TEST ITEM DETAILS

1% concentrate of Pirimiphos-methyl in Entostat (w/w) was produced at Exosect. Wax was heated in a copper pan and added to an over-head stirrer set to 600 rpm. Pirimithos-methyl was then added slowly under stirring. Stirring was continued for 5 min before pouring the liquid onto a metal tray and allowing to cool. Generally, the particles of wax of use in a dry powder composition of the invention possess a volume mean diameter of a selected size. To obtain particles of wax loaded with pirimithos-methyl of a volume mean diameter applicable for use in the invention, wax in the form of cooled down blocks, for example, 1 to 5 kilogram blocks or tablets may be broken up or kibbled into small millimeter-sized pieces (such as from 2 mm-8 mm approximate diameter in size, for example from 4 mm to 6 mm) in a kibbling machine. The millimeter-sized pieces can then be passed through a comminuting means such as a standard mill, e.g. an Apex Comminuting mill, and milled or comminuted into particles having an approximate diameter in the range from 100 µm-500 µm, for example from 250 µm-300 µm. The micron-sized comminuted particles can then be passed through a micronising apparatus, such as an AFG micronising air mill to obtain particles of any desired VMD range, such as up to 40 µm, that is of use in the present invention. The skilled addressee will appreciate that such procedures for obtaining small particles are well known in the art. Dry powder compositions of the invention typically comprise particles having a volume mean diameter of ≥5 µm, for example of 10 µm, 11 µm, 12 µm, 13 µm, 14 µm, 15 µm up to 200 µm or any value there in between, for example from ≥10 µm to 100 µm; or from ≥10 µm to 40 µm; or from ≥10 µm to 30 µm or any desired volume mean diameter value in between.

3a. QC Analysis was Carried Out Alongside the Study Following the Protocol:

Summary

The active, Pirimiphos-Methyl is extracted from the wax matrix by ultrasonication into n-hexane and analysed by gas liquid chromatography utilising a 100% dimethyl polysiloxane phase column to achieve separation from the non-actives. Detection is by Micro Electron Capture Detector (µECD) and quantitation is by internal standard.

1. Reagents

| | | |
|---|---|---|
| 1.1. | n-hexane | HPLC grade |
| 1.2. | internal standard | Pentachloronitrobenzene |
| 1.3. | actives | Pirimiphos-Methyl analytical reference material |

2. Equipment and Apparatus 2.1. Gas Chromatograph

Capable of operating over the range 100 to 350° C. with a µECD and an inlet which can accommodate a fused silica capillary column and a deactivated glass liner for split injections.

2.2. Column

Fused silica 15 m, 0.25 mm id, 100% dimethyl polysiloxane film thickness 0.25 µm (Rxi-1 ms or equivalent). The column should be conditioned according to the manufacturer's recommendations before use.

2.3. Ultrasonic Bath

Heated to 40° C. to improve extraction.

2.4. Dispenser Capable of Repeatable Dispensing of 50 ml of Organic Solvent 2.5. General Laboratory Glassware Volumetric flasks, bottles, beakers, pipettes, etc.

Chromatographic Conditions

Equilibrate the system using the following conditions until a steady baseline is achieved:

| | |
|---|---|
| Column | Fused silica 15 m, 0.25 mm i.d. Rxi-1 ms or equivalent, film thickness 0.25 µm. |
| Detector | µECD 330° C. nitrogen make up gas: 60 ml/min (or as recommended by the manufacturer) |
| Inlet System | Split/Splitless Inlet at 250° C. Spit Ratio 40:1 Incorporating a pre-treated Split/Splitless liner Syringe Wash Solvent A: n-hexane Syringe Wash Solvent B: acetone |
| Injection Volume | 1 µl |

3. C Procedure

Work in a fume hood and away from other equipment, use Benchkote to protect the work surface from spillages of Pirimiphos-Methyl solutions and to contain the active and sample powder. Solution volumes and weighing amounts may be reduced in ratio if required but the resulting concentration must not change.

3.1. Preparation of internal standard solution

Weigh 0.01 g of pentachloronitrobenzene (PCNB) into a 100 ml volumetric flask, dissolve in and make to volume with extraction solvent. Transfer 10 ml into a 100 ml volumetric flask and make to volume with extraction solvent (0.01 mg/ml internal standard solution).

Initial: 60° C.
Hold for 2 min.
40° C. min$^{-1}$ to 350° C.
Hold for 10 min.

NB the detector response to PCNB is approx 100 x that of pirimiphos-methyl hence the amount of IS added is approx 100 times lower.

3.2. Preparation of calibration standard solution

NB The values stated below are based on a nominal loading of 10 mg/g of active with a 100% purity reference material. The calibration range is calculated to be approx. 80-120% of this value. If the purity of reference material is less than 100% or if the nominal loading of active in the sample is different or uncertain (e.g. in weathered samples) the calibration and AQC must be adjusted accordingly. Not also that the detector response to PCNB is approx 100 that of pirimiphos-methyl hence the amount of IS added is approx 100 times lower.

Calibration Standard Solution 1

Weigh accurately 0.1 g (to the nearest 0.1 mg) of the Pirimiphos-Methyl reference material into a 100 ml volumetric flask, dissolve in and make to volume with extraction solvent (1 mg/ml standard solution).

Calibration Standard Solution 2

Into a series of 50 ml volumetric flasks pipette 0.7 ml of 0.01 mg/ml internal standard solution and add to each sucessive flask 0.56, 0.63, 0.7, 0.77 and 0.84 ml of Calibration Standard Solution 1. Make up to volume with extraction solvent. Correct for the purity of the reference material and to calculate the exact concentration of the standard solution in ug/ml.

Preparation of Analytical Quality Control (AQC) solution.

Weigh acurately 0.1 g (to the nearest 0.1 mg) of the Pirimiphos-Methyl ( ideally this should be from a difference source to the technical material but due to the limited sources of actives this is not always possible, and made up by a different operator on a different day) into a 100 ml volumetric flask, dissolve in and make to volume with extraction solvent (1 mg/ml AQC solution).

3.3. Linearity

A linearity check may be made by examination of the calibration curve for the standards. Examine the curve and the correlation coefficient. Review the data if the r$^2$ value is <0.98.

3.4. Sample Extraction

Weigh accurately 70 mg (to the nearest 0.1 mg) prepared sample into a tared 60 ml bottle and record its weight. Add by dispenser 50 ml extraction solvent. Add by 0.7 ml of 0.01 mg/ml internal standard solution. Cap the bottle and shake vigourously for 5 seconds. Place in an ultrasonic bath heated to 40° C. and sonicate. Turn off the bath after 5 minutes, remove the bottles and shake each bottle vigourously to re-disperse the product. Return to the bath and continue to sonicate. Repeat every 5 mins until the 15 mins has elapsed.

3.5. Extraction AQC 3.6. On an analytical balance tare a 60 ml bottle, and weigh in 70 mg bare micronised carnuba wax (to the nearest 10 mg). Add by dispenser 50 ml of extraction solvent. Add by pipette 0.7 ml of AQC solution and 0.7 ml of 0.01 mg/ml internal standard solution. Cap the bottle and shake vigourously for 5 seconds. Place in an ultrasonic bath heated to 40° C. and sonicate. Turn off the bath after 5 minutes, remove the bottles and shake each bottle vigourously to re-disperse the product. Return to the bath and continue to sonicate. Repeat every 5 mins until the 15 mins has elapsed.

Remove bottles from the bath and leave to stand for a minimum of 2 hours for the wax to settle.

Correct for the purity of the reference material and to calculate the exact concentration of the aqcsolution in ug/ml.

3.7. Chromatographic Analysis

The chromatographic injection sequence should be as follows:

Blank run —extraction solvent
Calibration standards x 5
Sample solutions (max. 12)
AQC x 3
Calibration standard Low
Calibration standard High
Blank run (no injection) 30 min hold @ 350° C.

Calculation

3.7.1. Calibration

Construct a graph of peak area ratio PAR (AI peak area/peak area IS) (y axis) vs concentration (x axis) for the calibration standards use a linear trendline to find the line of best fit and display the coefficient of determination r$^2$ and the equation for the line y = mX + c. Review the data if the r$^2$ value is <0.98.

olumn oven

| | |
|---|---|
| Helium Carrier Gas | Constant pressure, 10 psi |
| Run time | Approximately 20 min. |
| Approximate Retention Times | Internal standard 6.6 min. Active 7.1 min. |

3.7.2. Samples $$\text{Pirimiphos-Methyl concentration mg/g} = \frac{(PAR - c) \times 50}{m \times \text{sample wt (mg)}}$$

Wherein:

PAR=peak area ratio c=constant m=slope

50=extraction solvent volume ml

3.8. AQC $$AQC \text{ Al concentraion mg/ml} = \frac{(PAR - c)}{m}$$

$$\text{Check that: } \frac{AQC \text{ Al concentration mg/ml} * 100}{\text{Calculated } AQC \text{ conc.}} = 100 \; +/- \; 5\%$$

If the AQC value lies outside the range 95-105%, review the data.

4. TEST SYSTEM

The beetles tested in this study were sawtoothed grain beetle *Oryzaephilus surinamensis*. All beetles were taken from a lab-susceptible strain maintained at Exosect, which were set up from cultures supplied by the Food and Environment Research Agency (FERA) in 2011.

*Oryzaephilus surinamensis* were maintained in cultures reared on rolled oats and wheatgerm in a ratio of 3:1, w/w at 22±1° C. and 40±5% relative humidity (RH). Unsexed adult beetles were used for the trial. Mating status and age were unknown.

The untreated grain used for the experiment was supplied by Herbiseed, Twyford, England.

5. TEST LOCATION

Bioassay room 2: Temperature was maintained between 25±1° C. (Howe, R. W., 1956). Temperature and relative humidity (RH) were measured hourly using a Lascar data logger.

6. EXPERIMENTAL DESIGN

The treatments applied to the grain are listed as follows. There were 5 replicates for each treatment:
1) 10 mg of Entostat containing 0.1 mg of Pirimiphos-methyl (1%) per 50 g of grain. This is equivalent to 200 ppm of the formulation in grain.
2) 5 mg of Entostat containing 0.05 mg Pirimiphos-methyl (0.5%) per 50 g of grain. This is equivalent to 100 ppm of the formulation in grain.
3) 1 mg of Entostat containing 0.01 mg Pirimiphos-methyl (0.1%) per 50 g of grain. This is equivalent to 20 ppm of the formulation in grain.
4) Untreated control

7. APPLICATION DETAILS AND REGIME

The treatments (adjusted based on sample size) were added to the grain in 250 g samples which were homogenised by hand in a glass conical flask sealed with parafilm to ensure a uniform coating of the grain. 5×50 g lots of each 250 g grain sample were placed into 5 clean glass pots per treatment.

The different quantities of 1% Pirimiphos-methyl in Entostat (w/w) used in the protocol were based upon the standard 200-500 g/1000 kg of 2% Actellic dust (also expressible as 200-500 ppm in grain) used in a standard grain silo (Actellic, 1982, p. 43), in order to give comparable results. The quantity of Entostat added to each 50 g sample of grain equates to 10 mg, 5 mg and 1 mg respectively, for each treatment.

Once the treatments were added to the grain, 20 mixed-sex adult beetles were added to each pot and covered with a piece of gauze held in place with an elastic band.

8. SAMPLING/MEASUREMENT REGIME

The beetles were monitored for mortality every 48 h for two weeks, or until ~95% mortality had been achieved. During analysis, each pot was tipped out onto a white tray and the number of dead beetles recorded. Death was defined as when beetles failed to respond to continuous physical agitation with forceps or a fine-tipped paintbrush. All beetles, grain and loose powder were tipped back into the sample pots using a glass funnel and the white trays. After the final mortality check, the contents of each pot were frozen then disposed of in the chemical waste bin.

9. STATISTICAL ANALYSIS

Due to the nature of the results, the $LT_{50}$ (time to kill 50% of individuals) could not be determined using univariate general linear models. One-way ANOVA and Tukey's HSD post-hoc tests were used to determine significant differences between the treatments.

Results

10. EXPERIMENTAL RESULTS

Analysis of the data across groups via one-way ANOVA ($F_{(3,16)}$=3.0069, p=0.05) indicates that there are significant differences in the data at the 5% level between treatments (F=835.9506).

Pair-wise comparison across groups using Tukey's HSD post-hoc tests indicate that the significant differences at the 5% level ($q_{(4,16)}$=4.05, α=0.05) occur between the control and each pirimiphos-methyl treatment (q=61.3333).

There are absolutely no significant differences between the 10 mg, 5 mg, and 1 mg pirimiphos-methyl treatments (q=0).

Raw Data

| Treatment | 1 | 2 | 3 | 4 | 5 | Mean | S. dev | Mean (%) | S. dev (%) |
|---|---|---|---|---|---|---|---|---|---|
| Control | 1 | 1 | 1 | 1 | 4 | 1.60 | 1.34 | 8 | 6.71 |
| 1 mg/50 g | 20 | 20 | 20 | 20 | 20 | 20.00 | 0.00 | 100 | 0.00 |
| 5 mg/50 g | 20 | 20 | 20 | 20 | 20 | 20.00 | 0.00 | 100 | 0.00 |
| 10 mg/50 g | 20 | 20 | 20 | 20 | 20 | 20.00 | 0.00 | 100 | 0.00 |

QC Analysis

| | |
|---|---|
| Analysis Result for Batch: | W2491-3 |
| Product: | 1% Pirimiphos Methyl in Entostat (w/w) |
| Total Nominal Loading (mg/g): | 10 |
| Formulation Code: | n/a |
| Date of Analysis: | 24 Jul. 2012 |
| Sequence File Name: | 120723 |

| Pirimiphos-methyl | | |
|---|---|---|
| | Result (mg/g) | Result of Nominal (%) |
| Average | 11.52 | 112 |

Results from the QC analysis show that the concentration of Pirimiphos-methyl is well within the expected range in the Entostat Powder used for the study.

Discussion

11. DISCUSSION

This study demonstrates that 1% Pirimiphos-methyl in Entostat (w/w) is highly efficacious over an exposure duration of 48 hours when uniformly distributed at 10 mg, 5 mg and 1 mg in 50 g of wheat grain (equivalent to 200 g, 100 g, and 20 g per 1000 kg of wheat grain).

The 1 mg/50 g samples in particular demonstrate the potential of 1% Pirimiphos-methyl in Entostat (w/w), as the application rate in grain is a tenth of that recommended for use with 2% conventionally applied Actellic Dust (Actellic, 1982, p. 43).

12. REFERENCES

Howe, R. W. (1956). The Biology of the two common storage species of Oryzaephilus (COLEOPTERA, CUCUJIDAE). *Annals of Applied Biology* 44: 341-355.

Imperial Chemical Industries. (1982). *Actellic: Pirimiphos-methyl Broad Spectrum Insecticide* ($2^{nd}$ ed.). Surrey, England: ICI.

EXAMPLES SECTION II

The protocols described in Examples Section I above are used in determining the efficacy of different concentrations of Pirimiphos-methyl (0.25% and 0.5%) in Entostat (w/w) when used against *Oryzaephilus surinamensis* in grain. Similar results are observed.

Efficacy of Different Concentrations of Pirimiphos-Methyl (0.25% and 0.5%) in Entostat (w/w) when Used Against *Oryzaephilus surinamensis* in Grain Study Outline Actellic is an organophosphate insecticide originally developed by Imperial Chemical Industries (now Syngenta) in 1967. It uses pirimiphos-methyl as its active ingredient. It is highly efficacious against a range of insect species (Actellic, 1982, p. 44) and up until recently has been successfully used for the control of insect pests in stored grain and a range of public health situations. New regulations have resulted in the withdrawal of support for Actellic due to concerns over mammalian toxicity, environmental persistence and operator overexposure. Therefore, any new formulations comprising active ingredient e.g. an insecticide such as Actellic, that demonstrate high efficacy at low concentration levels would prove desirable. It is an object of the present invention to provide formulations for treating seed that contain lower amounts of active ingredient than formulations described in the prior art.

Preliminary tests at Exosect have demonstrated that 286 mg of 1% pirimiphos-methyl in Entostat (w/w) achieved 100% mortality against *O. surinamensis* when evenly distributed onto a filter paper (90 mm Ø) within a petri dish. This initial work served as evidence that pirimiphos-methyl was still active within the Entostat formulation.

Following on from preliminary work, the influence of application rate in grain on the efficacy of 1% pirimiphos-methyl in Entostat (w/w) against *O. surinamensis* was examined. To gather this information, quantities of grain were treated with various amounts of powder and homogenised before the addition of the beetles. The beetles were maintained within the grain for two weeks or until ~95% mortality was achieved, with mortality checks at 48 hour time points. This study demonstrated that 1% pirimiphos-methyl in Entostat (w/w) is highly efficacious, after achieving 100% mortality across all treatments over an exposure duration of 48 hours when uniformly distributed at 200 ppm, 100 ppm, and 20 ppm in wheat grain in sub-samples of 50 g.

The purpose of the present study is to examine the influence of pirimiphos-methyl concentration in Entostat (w/w) on the mortality of *Oryzaephilus surinamensis* in grain. An application rate of 20 ppm in wheat grain is used.

Having established that an application rate of 20 ppm in wheat grain provided an acceptably uniform coating and resulted in 100% mortality at a 1% concentration (w/w), this study looked to investigate the influence of active ingredient concentration at the same rate. 0.25%, 0.5% and 1.0% were tested.

Methods

Test Item Details 0.25%, 0.5% and 1% pirimiphos-methyl was added to liquid carnauba wax and particles were micronised therefrom as described herein, resulting in particles wherein the pesticide is present at a weight of 0.25%, 0.5% and 1% of the weight of the particles. Wax was heated in a copper pan and added to an over-head stirrer set to 600 rpm. Pirimithos-methyl is then added slowly under stirring. Stirring continues for 5 min before pouring the liquid onto a metal tray and allowing to cool.

Batch numbers were: W2491-1 (0.25%), W2491-2 (0.50%), W2491-3 (1.00%)

Test System

The beetles tested in this study were sawtoothed grain beetle *Oryzaephilus surinamensis*. All beetles were taken from a lab-susceptible strain maintained at Exosect, which were set up from cultures supplied by the Food and Environment Research Agency (FERA) in 2011.

*Oryzaephilus surinamensis* were maintained in cultures reared on rolled oats and wheatgerm in a ratio of 3:1 w/w at 22±1° C. and 40±5% relative humidity (RH). Unsexed adult beetles were used for the trial. Mating status and age were unknown.

The untreated grain used for the experiment was supplied by Herbiseed, Twyford, England.

Test Location

Bioassay room 2: Temperature was maintained between 25±1° C. (Howe, R. W., 1956). Temperature and relative humidity (RH) were measured hourly using a Lascar data logger.

Experimental Design 0.25%, 0.5% and 1% pirimiphos-methyl in carnauba wax (Entostat) (w/w) and the blank Entostat were applied at a rate of 20 ppm in wheat grain (20 g/tonne). Therefore the quantity of Entostat added to each 50 g sample equates to 1 mg. The treatments applied to the grain are listed as follows. There were 5 replicates for each of the following treatments:

1) 1 mg of carnauba wax (Entostat) containing 10 μg of Pirimiphos-methyl (1% w/w) in 50 g of grain
2) 1 mg of carnauba wax (Entostat) containing 5 μg Pirimiphos-methyl (0.5% w/w) in 50 g of grain
3) 1 mg of carnauba wax (Entostat) containing 2.5 μg Pirimiphos-methyl (0.25% w/w) in 50 g of grain
4) 1 mg of blank carnauba wax (Entostat) in 50 g of grain (Vehicle control)
5) 50 g of grain (Untreated control)

Application Details and Regime

The treatments (adjusted based on sample size) were added to the grain in 250 g samples and homogenised by hand in a glass conical flask sealed with parafilm to ensure a uniform coating of the grain. 50 g sub-samples of grain were placed into 5 clean glass pots per treatment.

Once the treatments had been divided into sub-samples, 20 mixed-sex adult beetles were added to each pot and covered with a piece of gauze held in place with an elastic band.

Sampling/Measurement Regime

The beetles were monitored for mortality after 48 hours of exposure to the treatments. During analysis, each pot was tipped out onto a white tray and the number of dead beetles recorded. Death was defined as when beetles failed to respond to continuous physical agitation with forceps or a fine-tipped paintbrush. All beetles, grain and loose powder were tipped back into the sample pots using a glass funnel and the white trays were wiped down with 5% decon between checks. After the final mortality check, the contents of each pot were frozen for 24 h then disposed of in the chemical waste bin.

Statistical Analysis

One-way ANOVA and Tukey's HSD post-hoc tests were used to determine significant differences between treatments. Probit analysis was performed on mortality results, with adjustments for control mortality using Abbott's Formula (up to 20%), to estimate the $LC_{50}$.

Results

Experimental Results

Analysis of the data across groups via one-way ANOVA ($F_{(4, 20)}$=2.8661, p=0.05) indicates that there are significant differences in the data at the 5% level between treatments (F=252.2817).

Pair-wise comparison across groups using Tukey's HSD post-hoc tests indicate that there is no significant difference at the 5% level ($q_{(5, 20)}$=4.23, α=0.05) between the untreated control and the vehicle control (q=1.7975). There are however significant differences between the 0.25% treatment and the untreated control (q=15.8543), and the vehicle control (q=14.0567).

The untreated control is also significantly different to the 0.5%, 1.0% treatments (q=32.6293), as is the vehicle control against the same treatments (q=30.8321). There is no significant difference between the 0.5% and 1% pirimiphos-methyl in Entostat (w/w) treatments (q=0).

QC Analysis

| Analysis Results for Batch: W2491-1, 2, 3 Pirimiphos-Methyl in Entostat Product: (w/w) | Comment: | W2491-1 = 0.25% W2491-2 = 0.50% W2491-3 = 1.00% |
|---|---|---|

Pirimiphos-methyl

| | Result (mg/g) | Result (%) |
|---|---|---|
| W2491-1 | 2.47 | 96 |
| W2491-2 | 5.52 | 110 |
| W2491-3 | 11.53 | 115 |

Results from the QC analysis show that the concentration of pirimiphos-methyl in Entostat (w/w) is well within the expected range for all treatments used in the study.

Probit Analysis

Probit analysis returned probit values of 4.98 and 4.9 for the 0.25% pirimiphos-methyl in Entostat (w/w) treatment after correcting for both the untreated control and the vehicle control respectively. No other probit values could be determined due to the nature of the results, therefore the 0.5% treatment result was regarded as a 99% mortality to give a probit value of 7.33.

Using the regression method the $LC_{50}$ was calculated to give a $Log_{10}$ concentration of 0.407069 and therefore a concentration of 2.55 mg/g (0.255%) when using the mortality percentage corrected for the vehicle control. When using the untreated control, the regression method returned a $Log_{10}$ concentration of 0.395669 and therefore a concentration of 2.49 mg/g (0.249%). Obtained $LC_{50}$ values should be considered as marginal underestimations due to the methods used.

Discussion

This study shows that 0.249-0.255% pirimiphos-methyl in Entostat (w/w) is a good estimation of the $LC_{50}$ against *Oryzaephilus surinamensis* over an exposure duration of 48 hours ($LT_{50}$) when the powder is uniformly distributed at a rate of 20 ppm in wheat grain ($LD_{50}$).

This demonstrates the potential of ~0.25% pirimiphos-methyl in Entostat (w/w), as the application rate in grain is a tenth of that recommended for use with 2% Actellic Dust (Actellic, 1982, p. 43), which is eight times more concentrated in formulation. This unexpectedly represents an overall 80 fold reduction over conventional application rates in the field.

The $LT_{50}$ for the 0.5% and 1% treatments is well within the 48 hour exposure period (given an $LD_{50}$ of 20 ppm in grain).

REFERENCES

Howe, R. W. (1956). The Biology of the two common storage species of *Oryzaephilus* (*COLEOPTERA, CUCUJIDAE*). *Annals of Applied Biology* 44: 341-355.

Imperial Chemical Industries. (1982). *Actellic: Pirimiphos-methyl Broad Spectrum Insecticide* (2$^{nd}$ ed.). Surrey, England: ICI.

Raw Data

| Treatment | 1 | 2 | 3 | 4 | 5 | Mean | S. dev | Mean (%) | S. dev (%) |
|---|---|---|---|---|---|---|---|---|---|
| Control 1 | 0.00 | 3.16 | 1.00 | 2.00 | 0.00 | 1.23 | 1.36 | 6.16 | 6.80 |
| Control 2 | 1.00 | 2.11 | 2.22 | 1.00 | 5.00 | 2.27 | 1.64 | 11.33 | 8.18 |
| 0.25% | 8.42 | 11.00 | 13.33 | 10.00 | 9.00 | 10.35 | 1.94 | 51.75 | 9.68 |
| 0.50% | 20.00 | 20.00 | 20.00 | 20.00 | 20.00 | 20.00 | 0.00 | 100.00 | 0.00 |
| 1.00% | 20.00 | 20.00 | 20.00 | 20.00 | — | 20.00 | 0.00 | 100.00 | 0.00 |

NB: Control 1 represents the untreated control. Control 2 represents the vehicle control. In some cases data has been corrected to account for missing beetles. Also, due to a lack of insects available, 1 rep has been omitted from the 1.0% pirimiphos-methyl group. An artificial pseudo-result of 20.00 was used for rep 5 in that group in order to generate statistical data. This estimation for rep 5 was based on the mean results and variance in the other 4 reps in the data set.

Probit Analysis with Corrected Mortality (%) Using Abbott's Formula

| Conc. (mg/g) | Conc. Log$_{10}$ | Total Number | Mean Mortality | % Mortality | Corrected Mortality (C1) | Corrected Mortality (C2) | Probit (C1) | Probit (C2) |
|---|---|---|---|---|---|---|---|---|
| (C1) 0 | — | 20 | 1.23 | 6.158 | — | — | — | — |
| (C2) 0 | — | 20 | 2.27 | 11.33 | — | — | — | — |
| 2.47 | 0.39 | 20 | 10.35 | 51.75 | 48.5885212 | 45.591242 | 4.98 | 4.9 |
| 5.52 | 0.74 | 20 | 20 | 100 | 100 | 100 | 7.33* | 7.33* |
| 11.53 | 1.06 | 20 | 20 | 100 | 100 | 100 | 7.33* | 7.33* |

*As mentioned in the report, 0.5% and 1.0% pirimiphos-methyl in Entostat (w/w) were treated as giving a corrected mortality of 99% in order to return Probit values of 7.33. This allowed for the calculation of the LC$_{50}$, which as such should be considered as a marginal underestimation of the true LC$_{50}$.

NB: C1 represents Control 1, the untreated control. C2 represents Control 2, the vehicle control. Probit values for the controls were not generated due to the concentration (mg/g) being 0. Probit values for 0.5% and 1.0% Primiphos-methyl in Entostat (w/w) could not be generated due to the corrected mortality being 100% in both cases.

The invention claimed is:

1. A method for controlling a population of arthropod pests on growing crops and/or on produce thereof with dry particles, wherein each of the particles has a hydrophobic exterior at which the particle adheres to the cuticle of at least one species of an arthropod pest and wherein the particles include at least one pesticide, the pesticide being present in a weight of no more than 2% of the weight of the particles, the method comprising the steps of:
   i) collecting the particles in a dusting apparatus; and
   ii) applying the particles to the growing crop and/or to produce thereof.

2. The method according to claim 1, wherein the particles potentiate the action of the pesticide on target arthropod pests.

3. The method according to claim 1, wherein the pesticide is present at a weight from ≥0.1% to ≤2% of the weight of the particles.

4. The method according to claim 1, wherein the hydrophobic exterior of each of the particles is formed by a wax that has a melting point ≥40° C. and is selected from one or more species of waxes selected from the group consisting of natural waxes, synthetic waxes and mineral waxes.

5. The method according to claim 1, wherein the particles are made up of solid wax particles that are selected from one or more species of waxes selected from the group consisting of natural waxes, synthetic waxes and mineral waxes.

6. The method according to claim 5, wherein the wax is selected from carnauba wax, montan wax and a mixture thereof.

7. The method according to claim 1, wherein the pesticide is selected from the group consisting of pyrethroids, spinosyns, carbamates, gamma amino butyric acid (GABA) inhibitors, neonicotinoids, anthranilamides, formonetins, essential oils, insect growth regulators, organophosphates and a mixture of two or more thereof.

8. The method according to claim 1, wherein the at least one species of arthropod pest is selected from the group consisting of Saw-toothed Grain Beetle (*Oryzaephilus surinamensis*); Grain Weevil (*Sitophilus granarius*); Common Flour Mite (*Acarus siro*); Warehouse Moth (*Ephestia elutella*); Flour or Mill Moth (*Ephestia kuhniella*); Flour Beetles (*Tribolium* spp.); Rust-red Grain Beetle (*Cryptolestes ferrugineus*); Cosmopolitan Food Mite (*Glycyphagus destructor*); codling moth (*Cydia pomonella*); oriental fruit moth (*Grapholita molesta*); armyworms from *Spodoptera* spp.); cabbage looper (*Trichoplusia* ni); thrips (*Frankliniella* spp.), onion thrips (*Thrips tebeciv*); leafminers (*Uriomyza* spp.); Corn earworm (*Helicoverpa zea*); European cornborer (*Ostrinie nubilalis*); *Agrotis* spp.; Cotton Bollworms(*Helicoverpa* spp.); Soybean looper (*Pseudoplusia* includes); Apple maggot (*Rhagoletis pomonella*); Pear psylla (*Cacopsylla* spp.); Navel orangeworm (*Amyelois transitella*); Tree Nuts Codling moth; Crucifers Diamondback moth (*Plutella xylostella*); cabbage worms (*Pieris* spp.); Grape berry moth (*Lobesia botrana*); Cucurbits Pickleworm (*Diaphania* spp.); and psocids.

9. The method according to claim 1, wherein the one or more species of arthropod pest is selected from the group consisting of Saw-toothed Grain Beetle (*Oryzaephilus surinamensis*), Grain Weevil (*Sitophilus granarius*), Common Flour Mite (*Acarus siro*), Warehouse Moth (*Ephestia elutella*), Flour or Mill Moth (*Ephestia kuhniella*), Flour Beetles (*Tribolium* spp.), Rust-red Grain Beetle (*Cryptolestes ferrugineus*) and Cosmopolitan Food Mite (*Glycyphagus destructor*).

10. A population of dry particles in the form of a powder for controlling populations of arthropod pests, wherein each of the particles has a hydrophobic exterior at which the particle adheres to the cuticle of at least one species of an arthropod pest and wherein the particles include at least one pesticide, the pesticide being present at a weight ≥0.1% to ≤2% of the weight of the particles.

11. The population of particles according to claim 10, wherein the hydrophobic exterior of each of the particles is formed by a wax that has a melting point ≥40° C. and is selected from one or more species of waxes selected from the group consisting of natural waxes, synthetic waxes and mineral waxes.

12. The population of particles according to claim 10 or claim 11, wherein the particles are solid wax particles selected from one or more species of waxes selected from the group consisting of carnauba wax, bees wax, Chinese wax, shellac wax, spermaceti wax, candelilla wax, montan wax, castor wax, ouricury wax and rice bran wax.

13. The population of particles according to claim 10, wherein the particles are selected from carnauba wax, montan wax and a mixture thereof.

14. The population of particles according to claim 10, wherein the pesticide is selected from the group consisting of pyrethroids, spinosyns, carbamates, gamma amino butyric acid (GABA) inhibitors, neonicotinoids, anthranilamides, formonetins, essential oils, insect growth regulators, organophosphates and a mixture of two or more thereof.

15. A method for controlling an infesting population of grain storage arthropod pests in a grain storage area with dry particles, wherein each of the particles has a hydrophobic exterior at which the particles adhere to the cuticle of at least one species of an arthropod pest and wherein the particles include at least one pesticide, the pesticide being present in a weight of no more than 2% of the weight of the particles, the method comprising the steps of:
  i) collecting the particles in a dusting apparatus; and
  ii) applying the particles to the grain storage area.

* * * * *